(12) United States Patent
Elsner

(10) Patent No.: US 10,034,725 B2
(45) Date of Patent: Jul. 31, 2018

(54) CHANNEL FORMATION FOR THE FIXING ELEMENT OF A DENTAL SUPERSTRUCTURE AND METHOD OF MAKING THE SAME

(75) Inventor: Edvin Elsner, Szigetszentmiklos (HU)

(73) Assignee: Elsner LLC, Wilmington, DE (US)

( * ) Notice: Subject to any disclaimer, the term of this patent is extended or adjusted under 35 U.S.C. 154(b) by 93 days.

(21) Appl. No.: 14/349,324

(22) PCT Filed: Apr. 12, 2012

(86) PCT No.: PCT/HU2012/000026
§ 371 (c)(1),
(2), (4) Date: Jun. 13, 2014

(87) PCT Pub. No.: WO2013/050796
PCT Pub. Date: Apr. 11, 2013

(65) Prior Publication Data
US 2014/0349250 A1 Nov. 27, 2014

(30) Foreign Application Priority Data

Oct. 4, 2011 (HU) .................................. 1100214 U
Oct. 4, 2011 (HU) ...................................... 1100555

(51) Int. Cl.
*A61C 8/00* (2006.01)
*A61C 13/00* (2006.01)
(52) U.S. Cl.
CPC ............ *A61C 8/0089* (2013.01); *A61C 8/005* (2013.01); *A61C 8/0037* (2013.01);
(Continued)

(58) Field of Classification Search
CPC ........................... A61C 8/0048; A61C 8/0051
(Continued)

(56) References Cited

U.S. PATENT DOCUMENTS 758,750 A * 5/1904 Haldeman .............. A61C 13/30
433/221
5,116,225 A * 5/1992 Riera ..................... A61C 8/005
433/173

(Continued)

FOREIGN PATENT DOCUMENTS

EP 2289461 A1 3/2011
EP 2452650 A1 5/2012

(Continued)

OTHER PUBLICATIONS

European Patent Office, International Search Report, application PCT/HU2012/000026, dated Aug. 30, 2012, Rijswijk, Netherlands.

*Primary Examiner* — Ralph Lewis
(74) *Attorney, Agent, or Firm* — Jason D. Voight

(57) ABSTRACT

A dental superstructure defines a channel formation for the fixing element of a dental superstructure. The superstructure (1) is fixed to an implantation (3) integrated in the jaw bone by means of a fixing element (2). A channel (7) is formed in the superstructure (1). The axis line (8) of the channel (7) is shaped to follow an arc (9) whose radii pointing to given points of the axis line (8) diverge from the plane of the arc (9) by 0-5°. The channel (7) is shaped in such a manner that the sections determined by the planes perpendicular to its axis line (8) are circles with the same diameter with their centers on the axis line (8). In the method according to the invention a computer controlled device is used for forming the channel.

8 Claims, 2 Drawing Sheets

(52) U.S. Cl.
CPC ........ *A61C 8/0051* (2013.01); *A61C 13/0004* (2013.01); *A61C 8/0068* (2013.01)

(58) Field of Classification Search
USPC .................................................. 433/173, 174
See application file for complete search history.

(56) References Cited

U.S. PATENT DOCUMENTS

| | | | |
|---|---|---|---|
| 9,592,106 B2* | 3/2017 | Piasini | A61C 13/26 |
| 2008/0311544 A1* | 12/2008 | Lee | A61C 8/005 433/173 |
| 2010/0297583 A1* | 11/2010 | Benzon | A61C 8/0048 433/174 |
| 2011/0217675 A1* | 9/2011 | Farre Berga | A61C 8/005 433/172 |
| 2012/0246916 A1* | 10/2012 | Farre Berga | A61C 8/005 29/700 |
| 2014/0186797 A1* | 7/2014 | Haus | A61C 8/0001 433/173 |
| 2014/0349250 A1* | 11/2014 | Elsner | A61C 8/005 433/174 |

FOREIGN PATENT DOCUMENTS

| | | |
|---|---|---|
| KR | 20010091658 A | 10/2001 |
| WO | WO2009068559 A1 | 6/2009 |

\* cited by examiner

CHANNEL FORMATION FOR THE FIXING ELEMENT OF A DENTAL SUPERSTRUCTURE AND METHOD OF MAKING THE SAME

TECHNICAL FIELD

The invention relates to a dental superstructure and a method of forming a curved channel therein for a fixing element by using a computer-controlled device.

A dental superstructure is fixed, preferably through an intermediate piece (interface), to a dental implant integrated in the jaw bone by means of a fixing element through an outlet hole provided with a shoulder. To ensure the insertion of the fixing element, a channel is formed in the superstructure between an inlet hole formed in the superstructure at its side facing the oral cavity and the shoulder of the outlet hole. The outlet hole, having a diameter corresponding to a threaded part of the fixing element, is provided in another working process.

BACKGROUND ART

In dentistry, there is a need for replacing missing teeth by an attractive and aesthetic prosthesis. To satisfy this need, an artificial dental root made of tissue-friendly material has been developed. The artificial dental root is implanted into the jaw bone in order to keep the artificial tooth or teeth firmly in position. In most cases, the material of the implant is pure, unalloyed titanium. The artificial tooth or the set of teeth is screwed to the dental implant through a screw channel. In the prior art, the insertion direction of the screw and the screwing direction were the same, consequently the bore-hole passed through the outer, visible surface of the tooth. This made covering of the screw channel rather difficult. Therefore, a dental system is required in which the opening of the screw inserting channel is formed on a non-visible surface.

Patent application EP2289461A1, titled "Dental System," describes a dental superstructure in which a screw member is inserted into an aperture of a screw channel and a screw member seat with a second aperture for providing support to the head of the screw member during fixation of the dental superstructure to a spacer element or an implant through the second aperture. At least one part of a center line of the screw channel and a center line of the second aperture do not coincide.

In this "Dental System" solution, forming the channel is rather complicated. On the one hand, insertion of the screw is complicated because of the varying diameter of the channel, and on the other hand, the dental superstructure is unreasonably weakened.

U.S. Pat. No. 5,116,225 describes an angulated abutment system for affixing a dental prosthesis to an anchor implanted in the jaw bone. The dental prosthesis can be mounted axially offset from the axis of the implant. Two components of the abutment system allow the dental prosthesis to be adjusted in small angles of rotation.

This solution also takes measures to fix the superstructure from its side facing the oral cavity, but it uses a number of components, the production of which is complicated. Although the channel is formed to be straight, providing an opening from the direction of the dental implant is complicated because of the many intermediate component parts.

Patent application WO 2008/138852 describes an adapter for a dental implant with a conical connection recess in its upper part. The adapter comprises a threaded part for connection with the dental implant and a conical main body corresponding to a conical connection recess of the implant, a tool grip portion allowing for attachment of the adapter to the implant by using a tool, and a connection recess adapted for connection to a spacer element or a dental superstructure.

In the above solution, the spacer is provided with outer and inner threads and on the one hand, it is fixed in the implant, and on the other hand, the superstructure is fixed in it.

Typically, this type of spacer is not used any longer since in recent times superstructures have been screwed directly to the dental implants. For the sake of proper positioning of the superstructure, a suitable interface may be installed between the dental implant and the superstructure.

SUMMARY OF INVENTION

The aim of the present invention is to provide a dental superstructure having a simpler channel formed therein as compared to the prior art solutions, which can be implemented easily with today's technical background, which is efficient and the production of which can be automatized. It helps dentists in working faster thereby causing less inconvenience to patients.

It has been realized that by forming a screw channel extending along an arched center line in one process, the screw used for fixing the superstructure can be inserted easily into the channel formed in the superstructure. Installation may be made easier by forming a channel with a slightly spiral center line. This can be done in one working process by using a milling machine controlled by a computer. If a spherical cutter is used, the shoulder of the shouldered outlet hole facing the channel can be formed as a regular segment of a sphere into which the head of the fixing element can be fitted perfectly.

The bore-hole of the outlet hole makes it possible for the fixing element, with its lower end engaging with the shoulder being also shaped as a segment of a sphere, to take the proper position when the superstructure is fixed to a dental implant. Additionally, if the shank of the fixing screw is made thinner above the threaded part and the interface is provided with a threaded bore-hole corresponding to the threads of the screw, then before the superstructure is placed in, after installation of the screw, the interface can be driven through the threaded part of the screw. In this manner the fixing element cannot fall out. In known solutions, these interfaces have been only placed on the fixing element entailing the possible loss of the individual components. In case of a lower denture, keeping the interface in its proper place was problematic while in case of an upper denture, temporary fixing of the screws was problematic.

According to the present invention, a dental superstructure with a curved channel for receiving a fixing element is provided. The superstructure can be fixed to a dental implant integrated in the jaw bone by means of a fixing element through a shouldered outlet hole formed in the superstructure. To ensure the insertion of the fixing element, a channel is formed in the dental superstructure between an inlet hole formed in the superstructure at its side facing the oral cavity and the shoulder of the outlet hole. Advantageously, the outlet hole is bored into the superstructure from the side of the dental implant in another working process, before or after forming the channel, in such a manner that it has a diameter corresponding to the threaded part of the fixing element. The center line of the channel is shaped to follow an arc whose radii, which point to given points of the center line of the channel, diverge from the plane of the arc at most ±5%, that is, advantageously, the center line of the channel may represent a three-dimensional spiral, i.e. a right-handed or left-handed helical line instead of a two-dimensional arc. Further, the channel is shaped in such a manner that the cross-sections in the planes perpendicular to its center line are circles of the same diameter with their centers residing on the center line.

Advantageously, the fixing element is a screw having a shank portion between the screw head and the threaded part, the diameter of which shank is smaller than the diameter of the threaded part.

Preferably, the dental superstructure is fixed to a dental implant using an interface by means of a screw wherein threads corresponding to the threaded part of the screw are formed in the interface.

Advantageously, the channel is formed by means of a spherical cutter, the shank diameter of which is at most 60% of the cutter head diameter.

Also, according to the present invention, a method of forming a channel for a fixing element in a dental superstructure by using a computer-controlled device is provided. By means of a fixing element introduced through an inlet hole of the channel, the superstructure can be fixed, via a shouldered outlet formed in the superstructure, to the dental implant integrated into the jaw bone. Advantageously, the outlet hole is bored into the superstructure from the side of the implant in another working process, before or after forming the channel, in such a manner that it has a diameter corresponding to the diameter of the shank of the fixing element. Between the side of the superstructure facing the oral cavity and the shoulder of the outlet, a channel having a circular cross-section is formed by means of a spherical cutter. In this process, a bore-hole having a cross-section corresponding to the cross-section of the channel is formed in the superstructure, wherein the center line of the bore-hole forms an arc in such a manner that radii running from the center of the arc and pointing to given points of the center line of the bore-hole diverge from the plane of the arc by at most ±5%. It means that in a certain case, the center line of the channel is formed to be helical.

Further, the channel may be shaped in such a manner that its cross-sections in the planes perpendicular to its center line are circles of the same diameter with their centers residing on the center line.

Advantageously, the channel is formed by means of a spherical cutter, the shank diameter of which is at most 60% of the cutter head diameter.

Preferably, the dental superstructure is fixed to a dental implant by means of a fixing element, which has a shank between its head and its threaded part, said shank portion having a smaller diameter than the diameter of the threaded part.

Advantageously, the superstructure is fixed to a dental implant through an interface, in which threads are formed corresponding to the threaded part of the screw.

BRIEF DESCRIPTION OF DRAWINGS

A detailed description of the invention will be given with reference to the accompanying drawings in which.

DESCRIPTION OF EMBODIMENTS

Figure 1:
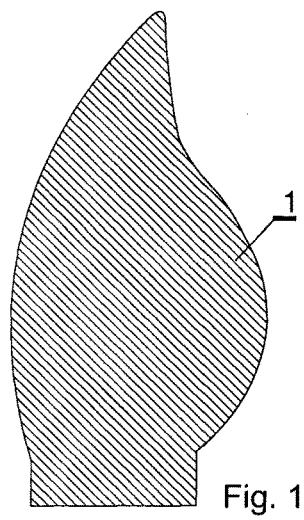
FIG. 1 is a side view showing the cross-section of a blank dental superstructure.
Figure 2:
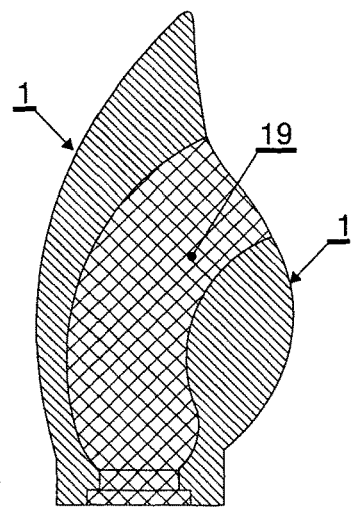
FIG. 2 is a cross-sectional side view showing the a metal-sintered dental superstructure, into which a spatial mesh framework of the channel and the outlet is inserted during the method of forming a channel is shown.
Figure 9:
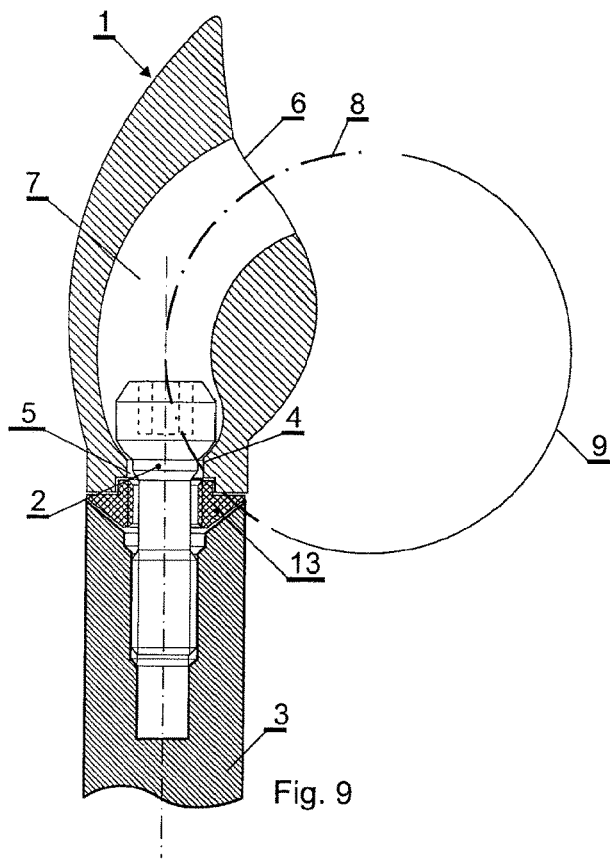
FIG. 9 is a partial cross-sectional side view of the superstructure mounted on a dental implant with an inserted interface, wherein the fixing element is depicted in side view.

With the present invention, a channel 7 is formed in a dental superstructure 1 for an aesthetical attachment of the dental superstructure shown in FIG. 1 to a dental implantat. An inlet 6 is formed on a side of the superstructure 1 facing the oral cavity. (In case of a superstructure 1 comprising a number of false teeth it is not necessary to form a channel 7 in each of the false teeth.) In this manner, when the superstructure 1 and the dental implant 3 are fixed together by means of a fixing element 2, the filling material used for covering the inlet 6 of the channel 7 will not be seen after the superstructure 1 is mounted on. In addition, the filling material will not appear on the occlusal surface of a false tooth. Typically, forming this type of channel 7 can be important mainly in the case of front teeth (FIG. 9).

Figure 5:
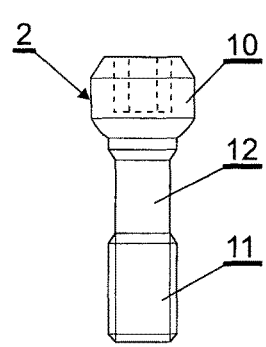
FIG. 5 is a side view of a possible embodiment of a fixing element.

Advantageously, in the simplest and most efficient way, the channel 7 is formed in the superstructure 1 by a computer-controlled device. The fixing element 2 may be inserted into the channel 7 formed in superstructure 1. The channel 7 is provided with an inlet 6 facing the oral cavity. It has a diameter large enough to receive a fixing element 2, which, in this example, is an Allen screw (FIG. 5). The fixing element 2 comprises a head 10, a threaded part 11 and a shank portion 12. In the superstructure 1, the channel 7 extends to the shoulder 4 of outlet 5. The shoulder 5 provides a seat for the head 10 of the fixing element 2. The threaded part 11 and a major part of the shank portion 12 of the fixing element 2 are driven out through the outlet 5 of the channel 7 before the superstructure 1 is mounted on. The head 10 of the fixing element 2 is seated on the inner side of the shoulder 4, which may be shaped as a segment of a sphere. The surface of the head 10 of the fixing element 2 facing the shoulder 4 may also be shaped as a segment of a sphere. The outlet 5 is bored into the superstructure 1 from the side of the dental implant 3 in another working process, before or after forming the channel 7, in such a manner that it has a diameter corresponding to the diameter of the threaded part 11 of the fixing element 2.

Figure 7:
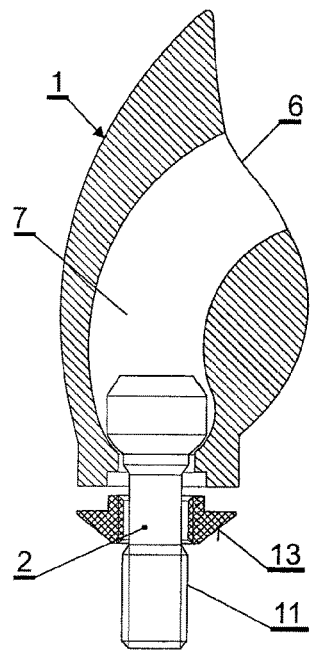
FIG. 7 is a cross-sectional side view of a superstructure and an interface showing the assembled superstructure before it is fixed to a dental implant.
Figure 8:
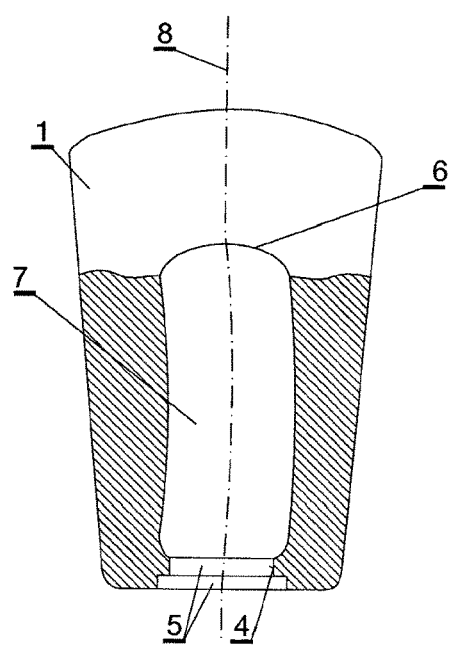
FIG. 8 is a rear view of the cross-section of an element of the superstructure in case of a helically formed channel.

According to the present invention, the center line 8 of the channel 7 forms a part of a circular arc 9. The circular arc 9, defining the center line 8 of the channel 7, may also be formed in such a manner that it diverges from its own plane by a few degrees, at most by ±5 degrees. In this manner, a slightly diverging spiral path is produced along the periphery of the circular arc 9 (FIG. 8). That is, advantageously, the center line 8 represents a three-dimensional spiral line, a right-handed or left-handed helical line instead of a two-dimensional arc. The cross-section of the channel 7 is essentially constant. It narrows only at the outlet 5 to have a diameter corresponding to the diameter of the outlet 5 (FIG. 7).

The fixing element 2 is a screw having a shank portion 12 between its head 10 and its threaded part 11, wherein the diameter of said shank portion 12 is smaller than the diameter of the threaded part 11.

Figure 6:
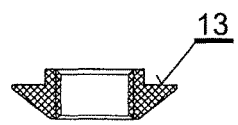
FIG. 6 shows the cross-section of a possible embodiment of an interface.

In many cases, an interface 13 (FIG. 6) is located between the superstructure 1 and the dental implant 3, which are fixed together by means of a fixing element 2. In order to make mounting of the superstructure 1 onto the dental implant 3 easier, threads corresponding to the threaded part 11 of the fixing element 2 are formed in the interface 13. Thus, after insertion of the fixing element 2 into the superstructure 1, the interface 13 can be driven through the threaded part 11 of the fixing element 2 onto the shank portion 12. In this manner both the interface 13 and the fixing element 2 are prevented from falling out when the superstructure 1 is mounted on a dental implant 3. At the same time, insertion of the fixing element 2 into the dental implant 3 is not inhibited by the interface 13.

Figure 3:
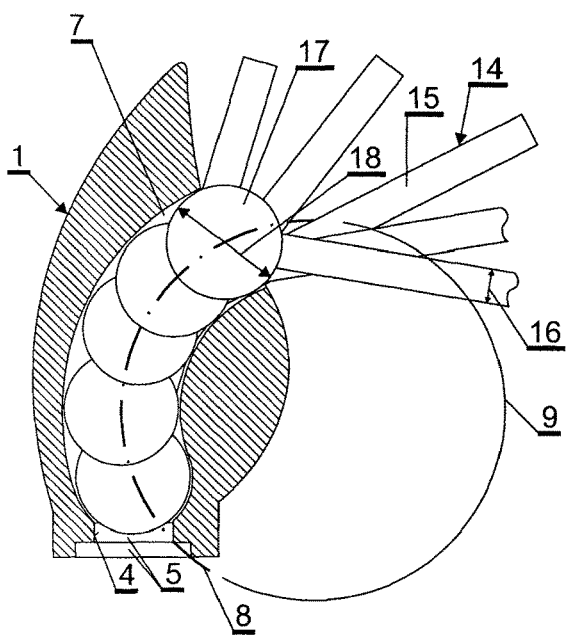
FIG. 3 is a cross-sectional side view of the superstructure showing a number of positions of the spherical cutter during process of forming a channel.
Figure 4:
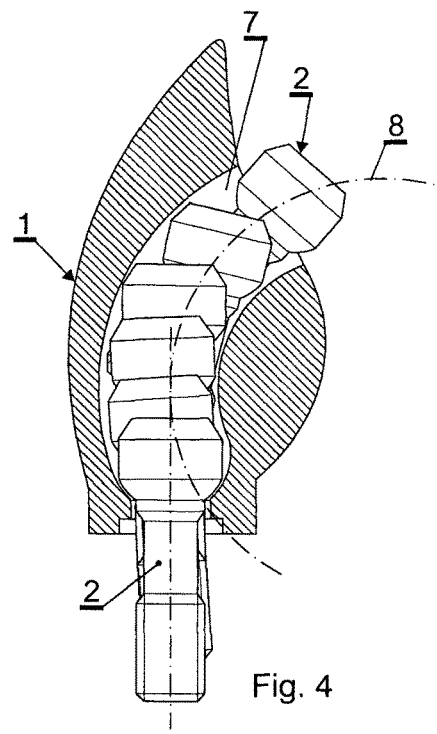
FIG. 4 is a cross-sectional side view of the superstructure showing the process of inserting the fixing element into the channel.
Figure 10:
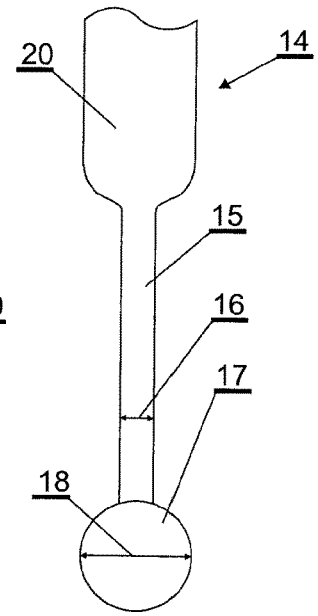
FIG. 10 shows the side view of a possible embodiment of a spherical cutter.

To form the channel 7, a spherical cutter 14 is used. The cutter head is not necessarily ball-shaped, it can be dome-shaped, or it may have the shape of a segment of a sphere. The cutter head 17 of the spherical cutter 14, used in the present invention, is preferably ball-shaped. In the present example, the diameter 16 of the shank 15 of the spherical cutter 14 is 30% of the diameter of the cutter head 18 (FIG. 3). The end 20 of the shank 15 can be fixed in the computer-controlled device (FIGS. 3 and 10). The path, along which the cutter head 17 advances, is also shown in FIG. 3, while FIG. 4 shows the travel of the fixing element 2 in the channel 7 during its insertion.

Dental implants can be produced with great accuracy in a highly productive metal sintering method. Much material and work can be saved during the manufacture if a spatial mesh framework 19 is formed in the space of the channel 7. The spatial mesh framework 19 ensures that a satisfactorily dense material can be built on the other parts of the implant 3. Considering that the material used for making the implant is very expensive, this solution may result in significant material savings. Between the frame elements of the spatial mesh framework 19, the space angle is 30 degrees. This framework ensures the required static structure and accuracy. Removal of these supporting elements can be done on completion of the metal sintering method as described previously.

According to the invention, the method of forming a channel 7 for receiving a fixing element 2 in dental superstructure 1 is accomplished by means of a computer-controlled device. During the method, a channel 7 with a circular cross-section is formed from the side of the superstructure 1 facing the oral cavity to the shoulder 4 of outlet 5 by means of a spherical cutter 14 (FIG. 3). To this end, a bore-hole having a cross-section corresponding to the cross-section of the channel 7 is formed in the superstructure 1, wherein the center line 8 of the bore-hole defined by a circular arc 9 in such a manner that radii running from the center of the arc 9 and pointing to given points of the center line 8 of the bore-hole diverge from the plane of the arc 9 by at most ±5 percent. It means that, in a certain case, the center line 8, as well as the channel 7 is formed to be helical (FIG. 8). The axis of the threaded bore-hole formed in the dental implantat 3 is tangent to the center line 8. Furthermore, the channel 7 is shaped in such a manner that the cross-sections in the planes perpendicular to its center line 8 are circles of the same diameter with their centers residing on the center line 8.

To form the channel 7, a spherical cutter 14 is used. The diameter of the shank 15 of the spherical cutter 14 is at most 60%, preferably only 30% of the diameter of the cutter head 18.

The dental implant 3 can be made of any biologically compatible metal or ceramic material. Usually, the material of the superstructure 1 is zirconium (Zr), cobalt-chrome alloy, titanium, etc. Of course, any kind of material used in dental technology may be suitable.

The outlet 5 can be formed on the surface of the superstructure 1 facing the dental implant 3 by a simple boring process. To cut the channel 7, a high precision five-axis milling machine may be used with a spherical cutter 14, which is driven along a two- or three-dimensional (spiral) path. Shaping is carried out by means of a cutter-head 17 having a shank 15 with a diameter 16 smaller than the diameter of the cutter head 18. This makes it possible that concave, so-called undercut surfaces, can be shaped from the direction of work.

Then the fixing element 2 can be inserted easily into the channel 7.

According to an embodiment of the present invention, the screwing direction and the screw insertion direction are on the same arc. The two- or three-dimensional (spiral) path tangent to the central axis of the dental implant at the same time corresponds to the screw insertion direction. Consequently, any unnecessary procedure, which would weaken the dental implant, can be avoided and a statically stronger superstructure can be obtained as compared to the known superstructures, in which some portions of the channel were significantly widened. The embodiments according to the present invention provide a high-level solution both in terms of aesthetics and assembly technique. It is aesthetic since the inlet of the channel cannot be seen when the person wearing superstructure is talking. In respect of the assembly technique, the solution according to the present invention makes it possible for a dentist to screw a dental implant to its place by means of a device tilted towards the oral cavity. In this case, the opposing row of teeth does not interfere with the screwing operation.

The invention claimed is:

1. A dental superstructure comprising a channel extending through the superstructure from an inlet of the superstructure to an outlet thereof,
   wherein said channel comprises an arcuate channel section and a straight channel section:
      said arcuate channel section starting from said inlet and having an inner end at a location inside the superstructure, said arcuate channel section having a curved center line along an entire length of the arcuate channel section, wherein said arcuate channel section has, along its entire length, a circular cross-section with a first circular cross-sectional area in any plane perpendicular to its center line, and
      said straight channel section extending between the inner end of the arcuate channel section and said outlet of the superstructure, said straight channel section having a straight center line tangent to the center line of the arcuate channel section and having a second cross-sectional area being smaller than said first circular cross-sectional area except at the inner end of the arcuate channel section, and wherein a shoulder is formed at the inner end of the arcuate channel section, and wherein said first circular cross-sectional area is essentially constant over the entire length of the arcuate channel section except for narrowing at the inner end of the arcuate channel section to correspond to the second cross-sectional area.

2. The dental superstructure of claim 1, wherein the center line of said arcuate channel section is circular and running within a plane along the entire length of the arcuate channel section.

3. The dental superstructure of claim 1 having only a single said channel.

4. The dental superstructure of claim 1 wherein an inner side of the shoulder is shaped as a segment of a sphere.

5. A method of forming a channel in a solid dental superstructure, said method comprising the steps of:

forming an arcuate channel section in the solid superstructure using a first boring tool with starting from an inlet of the channel, said arcuate channel section extending between said inlet of the superstructure and an inner end thereof at a location inside the superstructure, said arcuate channel section having a curved center line along an entire length of the arcuate channel section, and wherein said arcuate channel section has, substantially along its entire length, a circular cross-section with a first circular cross-sectional area in any plane perpendicular to its center line, and forming a straight channel section in the solid superstructure extending between an outlet of the superstructure and said inner end of the arcuate channel section using a second boring tool with starting from the outlet of the superstructure, said straight channel section having a straight center line tangent to the center line of the arcuate channel section and wherein said straight channel section has a second cross-sectional area smaller than said first circular cross-sectional area except at the inner end of the arcuate channel section, and narrowing said first cross-sectional area only at the inner end of the arcuate channel section to correspond to the second cross-sectional area.

6. The method of claim 5, wherein the arcuate channel section is formed to have a circular center line running within a plane along the entire length of the arcuate channel section.

7. The method according to any one of claim 5, wherein the first boring tool is a spherical cutter having a cutter head and a shank, wherein the diameter of the shank is at most 60% of the diameter of the cutter head.

8. The method of claim 5 wherein said first boring tool is a spherical cutter such that the inner end of the arcuate channel narrows in the shape of a segment of a sphere.

* * * * *